(12) United States Patent
Chen et al.

(10) Patent No.: US 12,012,482 B1
(45) Date of Patent: Jun. 18, 2024

(54) BIO-BASED MOISTURE ABSORPTION AND SWEAT DISCHARGING MULTIFUNCTIONAL FINISHING AGENT AND PREPARATION METHOD AND APPLICATION THEREOF

(71) Applicant: Zhangjiagang Duplus Chemical Co., Ltd., Jiangsu (CN)

(72) Inventors: Jinhui Chen, Jiangsu (CN); Yuchun Wu, Jiangsu (CN); Jun Chen, Jiangsu (CN); Weiwei Shao, Jiangsu (CN)

(73) Assignee: ZHANGJIAGANG DUPLUS CHEMICAL CO., LTD., Jiangsu (CN)

( * ) Notice: Subject to any disclaimer, the term of this patent is extended or adjusted under 35 U.S.C. 154(b) by 0 days.

(21) Appl. No.: 18/236,612

(22) Filed: Aug. 22, 2023

(30) Foreign Application Priority Data

Mar. 30, 2023 (CN) .......................... 202310323820.3

(51) Int. Cl.
*D06M 15/51* (2006.01)
*A61K 8/85* (2006.01)
*C08G 63/16* (2006.01)

(52) U.S. Cl.
CPC ................ *C08G 63/16* (2013.01); *A61K 8/85* (2013.01)

(58) Field of Classification Search
None
See application file for complete search history.

(56) References Cited

FOREIGN PATENT DOCUMENTS

| CN | 101265664 A | 9/2008 |
|---|---|---|
| CN | 104603175 A | 5/2015 |
| CN | 110483749 A | 11/2019 |
| CN | 111286012 A | 6/2020 |
| CN | 114539512 A | 5/2022 |
| CN | 114752046 A | 7/2022 |
| KR | 20140088972 A | 7/2014 |

*Primary Examiner* — Nicole P Babson
*Assistant Examiner* — Lori K Mattison
(74) *Attorney, Agent, or Firm* — Schmeiser, Olsen & Watts, LLP

(57) ABSTRACT

A bio-based moisture absorption and sweat discharging multifunctional finishing agent and a preparation method and application thereof is provided, a structural formula of which is:

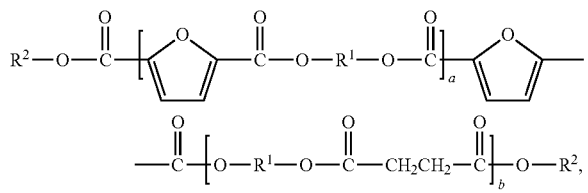

wherein, $R^1$ is linear or branched alkyl; $R^2$ is derived from bio-based polyethylene glycol, with a molecular structure of —$(CH_2CH_2O)_n$—H, n=22~91, and n is a natural number; a=60~150, and a is a natural number; b is a natural number; the molar ratio of structural units with a degree of polymerization of a to those with a degree of polymerization of b is (30~85):(15~40). Its use in the after finish of hydrophobic fiber fabrics can improve their water absorption and anti-static properties, giving them a laundering durable effect and a fluffy and soft feel.

13 Claims, No Drawings

BIO-BASED MOISTURE ABSORPTION AND SWEAT DISCHARGING MULTIFUNCTIONAL FINISHING AGENT AND PREPARATION METHOD AND APPLICATION THEREOF

CROSS REFERENCE TO RELATED APPLICATIONS

This application claims the benefit of Chinese Patent Application No. 202310323820.3, filed on Mar. 30, 2023, the contents of which are incorporated by reference herein.

FIELD OF TECHNOLOGY

The following relates to the chemical engineering field, and particularly relates to a bio-based moisture absorption and sweat discharging multifunctional finishing agent and a preparation method and application thereof.

BACKGROUND

Polyester fiber is a typical hydrophobic fiber with a standard moisture regain of only 0.4%, however, its drip diffusion time is >180 s, its hydrophilic capillary effect value is ≤50 mm/30 min, and it is prone to generating static electricity when rubbing, has poor hand feel, and is easy to stain, which limits its use. To this end, various finishing agents have been invented to improve the clothing performance of polyester fiber fabrics.

At present, in publicly available conventional art, it is usually to introduce linear or branched polyethylene glycol hydrophilic groups into the main chain of polyester (polydimethyl terephthalate) to improve the hydrophilicity of polyester fibers, which can achieve good results, however, regardless of which structure of polyethylene glycol chain segment is embedded, it can only improve or enhance the hydrophilicity of polyester fabrics, and cannot contribute to their laundering durability. According to the principle of similar miscibility, polyester chain segments undergo eutectic melting with polyester fiber chain segments during high-temperature setting, forming a stable structure, achieving laundering durability and fluffy and soft hand feel. However, numerous studies have proved that excessive addition of polyether hydrophilic chain segments, especially embedding of polyethylene glycol hydrophilic chain segments with irregular macromolecular side chains, will hinder the eutectic melting of polyester chain segments and polyester fabrics, affecting their laundering durability, making the finished fabric unable to balance hydrophilicity and laundering durability.

SUMMARY

An aspect relates to a bio-based moisture absorption and sweat discharging multifunctional finishing agent and a preparation method and application thereof, hydrophobic fiber fabrics treated with this finishing agent have excellent moisture absorption, sweat discharging, hydrophilicity, antistatic properties, soft and fluffy hand feel, and laundering durability, enabling them to achieve multiple functions in one finish.

To achieve the above aspect, a technical solution employed by the present disclosure is as follows:

A first aspect of the present disclosure provides a bio-based moisture absorption and sweat discharging multifunctional finishing agent, which has a structural formula of:

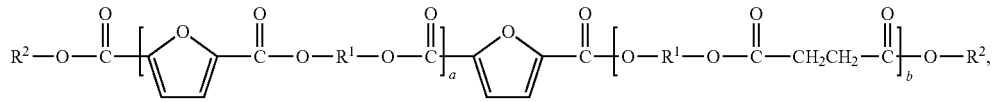

wherein, $R^1$ is linear or branched alkyl;

$R^2$ is derived from bio-based polyethylene glycol, with a molecular structure of $—(CH_2CH_2O)_n—H$, n=22 to 91, and n is a natural number;

a=60 to 150, and a is a natural number, for example, 60, 70, 80, 90, 100, 110, 120, 130, 140, 150;

b is a natural number;

the molar ratio of structural units with a degree of polymerization of a to those with a degree of polymerization of b is (30 to 85):(15 to 40).

Further, the molecular structure of $R^1$ is $—(CH_2)_c—$, c=2 to 4, c is a natural number, for example, $—CH_2—CH_2—$, $—CH_2—CH_2—CH_2—$, $—CH_2—CH_2—CH_2—CH_2—$.

Further, the molecular structure of $R^1$ in the structural units with a degree of polymerization of a is the same as or different from that of the structural units with a degree of polymerization of b; different.

Further, $R^1$ is derived from a corresponding bio-based diol, and the molecular structure of the bio-based diol is $HO—(CH_2)_c—OH$, c=2 to 4, c is a natural number, for example, $HO—CH_2—CH_2—OH$, $HO—CH_2—CH_2—CH_2—OH$, $HO—CH_2—CH_2—CH_2—CH_2—OH$.

Further, in the structural formula of the bio-based moisture absorption and sweat discharging multifunctional finishing agent, the molar ratio of structural units with a degree of polymerization of a to those with a degree of polymerization of b is (30 to 80):(20 to 40).

Further, the bio-based moisture absorption and sweat discharging multifunctional finishing agent after polymerization has a weight-average molecular weight of 8000 to 30000 g/mol.

In an embodiment, the bio-based moisture absorption and sweat discharging multifunctional finishing agent after polymerization has a weight-average molecular weight of 10000 to 25000 g/mol.

Further, in the structural formula of the bio-based moisture absorption and sweat discharging multifunctional finishing agent, the structural units with a degree of polymerization of a and a degree of polymerization of b are blocked, alternately, or statistically distributed.

In an embodiment, the raw materials for the preparation of the bio-based moisture absorption and sweat discharging multifunctional finishing agent comprises: a bio-based dibasic acid or ester containing a furan structure, a bio-based aliphatic dibasic acid or ester, a bio-based diol, and bio-based polyethylene glycol.

According to a specific implementation, the bio-based dibasic acid or ester containing a furan structure is bio-based 2,5-furandicarboxylic acid or bio-based dimethyl furan-2,5-dicarboxylate, and the bio-based aliphatic dibasic acid or ester is bio-based succinic acid or bio-based dimethyl succinate.

In an embodiment, the bio-based dibasic acid or ester containing a furan structure, the bio-based aliphatic dibasic acid or ester, the bio-based diol and the bio-based polyethylene glycol are all obtained from bio-based materials through fermentation, purification and certain chemical conversion.

In this application, the preparation of the bio-based dibasic acid or ester containing a furan structure, the bio-based aliphatic dibasic acid or ester, the bio-based diol and the bio-based polyethylene glycol are all mature conventional art, which will not be repeated here.

In an embodiment, the bio-based diol is selected from the group consisting of bio-based 1,3-propanediol, bio-based ethylene glycol, bio-based 1,4-butanediol, and combinations thereof.

Further, the bio-based diol comprises at least bio-based ethylene glycol.

Further, the bio-based diol further comprises bio-based 1,3-propanediol or bio-based 1,4-butanediol.

According to an embodiment, the bio-based diol is bio-based ethylene glycol and bio-based 1,3-propanediol.

Further, the feeding weight ratio of the bio-based ethylene glycol to the bio-based 1,3-propanediol is 1:(0.6 to 2.5); 1:(0.8 to 2.2); further optimized as 1:(1 to 2.0).

According to an embodiment, the bio-based diol is bio-based ethylene glycol and bio-based 1,4-butanediol.

Further, the feeding weight ratio of the bio-based ethylene glycol to the bio-based 1,4-butanediol is 1:(0.5 to 3); 1:(1 to 2.5); further optimized as 1:(1 to 2.25).

In an embodiment, the bio-based polyethylene glycol is bio-based polyethylene glycol with a weight-average molecular weight of 1000 to 4000 g/mol; bio-based polyethylene glycol with a weight-average molecular weight of 2000 to 4000 g/mol.

According to a specific implementation, the bio-based polyethylene glycol can be selected from PEG1000, PEG1500, PEG2000, PEG3000, PEG4000, etc.; PEG2000 or PEG4000.

A further aspect of the present disclosure provides a preparation method of a bio-based moisture absorption and sweat discharging multifunctional finishing agent, which comprises steps of:

(1) reacting a bio-based dibasic acid or ester containing a furan structure, a bio-based aliphatic dibasic acid or ester, a bio-based diol with bio-based polyethylene glycol under the action of a catalyst to obtain a transesterification prepolymer product;

(2) making the transesterification prepolymer product obtained in step (1) under evacuation to undergo a polycondensation reaction to give the bio-based moisture absorption and sweat discharging multifunctional finishing agent;

in step (1), the bio-based polyethylene glycol is added in the same procedure with the bio-based dibasic acid or ester containing a furan structure, the bio-based aliphatic dibasic acid or ester and the bio-based diol to react to give the transesterification prepolymer product;

or, the bio-based polyethylene glycol is added after the bio-based dibasic acid or ester containing a furan structure, the bio-based aliphatic dibasic acid or ester and the bio-based diol are reacted to obtain an intermediate product, and then the reaction continues to give the transesterification prepolymer product.

According to a specific implementation, the preparation method of a bio-based moisture absorption and sweat discharging multifunctional finishing agent specifically comprises:

step I: reacting a bio-based dibasic a containing a furan structure, a bio-based aliphatic dibasic acid or ester and a bio-based diol under the action of a catalyst to obtain an intermediate product;

step II: performing a transesterification reaction between bio-based polyethylene glycol and the intermediate product obtained in step I under the action of a catalyst to obtain a transesterification prepolymer product;

step III: making the transesterification prepolymer product obtained in step II under evacuation to undergo a polycondensation reaction to give the bio-based moisture absorption and sweat discharging multifunctional finishing agent.

In an embodiment, the feeding weight ratio of the bio-based dibasic acid or ester containing a furan structure, the bio-based aliphatic dibasic acid or ester, the bio-based diol, and the bio-based polyethylene glycol is 1:(0.1 to 2):(0.9 to 3.6):(5 to 40).

Further, the feeding weight ratio of the bio-based dibasic acid or ester containing a furan structure, the bio-based aliphatic dibasic acid or ester, the bio-based diol, and the bio-based polyethylene glycol is 1:(0.1 to 0.5):(1 to 1.7):(8 to 16).

Further, the feeding weight ratio of the bio-based dibasic acid or ester containing a furan structure, the bio-based aliphatic dibasic acid or ester, the bio-based diol, and the bio-based polyethylene glycol is 1:(0.15 to 0.49):(1.4 to 1.7):(12 to 16).

In an embodiment, the reaction in step I is controlled at a temperature of 150 to 220° C. for 3 to 5 hours.

Further, the reaction in step I is controlled at a temperature of 150 to 180° C. for 1 to 2 hours, followed by a further increase in temperature to 190 to 220° C. for 2 to 3 hours.

Further, the reaction in step I is controlled at a temperature of 165 to 180° C. for 1 to 1.5 hours, followed by a further increase in temperature to 200 to 210° C. for 2 to 2.5 hours.

In an embodiment, the transesterification reaction in step II is controlled at a temperature of 180 to 250° C. for 2 to 5 hours.

Further, the transesterification reaction in step II is controlled at a temperature of 200 to 220° C. for 1 to 2 hours, followed by a further increase in temperature to 230 to 250° C. for 1.5 to 3 hours.

Further, the transesterification reaction in step II is controlled at a temperature of 210 to 220° C. for 1 to 1.5 hours, followed by a further increase in temperature to 240 to 245° C. for 1.5 to 2 hours.

In an embodiment, the polycondensation reaction in step III is controlled at a temperature of 240 to 280° C. and a vacuum degree of 0.05 to 0.1 MPa for 3 to 5 hours.

Further, the polycondensation reaction in step III is controlled at a temperature of 250 to 270° C. and a vacuum degree of 0.06 to 0.1 MPa (for example, 0.06 MPa, 0.065 MPa, 0.07 MPa, 0.075 MPa, 0.08 MPa, 0.085 MPa, 0.09

MPa, 0.095 MPa, 0.1 MPa) for 3 to 4.5 hours (for example, 3 hours, 3.5 hours, 4 hours, 4.5 hours).

Further, the polycondensation reaction in step III is controlled at a temperature of 260 to 265° C. and a vacuum degree of 0.095 to 0.1 MPa for 3 to 3.5 hours.

In an embodiment, the catalyst is an acetate metal salt catalyst and/or an organic titanate catalyst.

Further, the acetate metal salt catalyst is zinc acetate and/or sodium acetate.

Further, the organic titanate catalyst is selected from the group consisting of tetramethyl titanate, tetraethyl titanate, tetrapropyl titanate, tetraisopropyl titanate, tetrabutyl titanate, and combinations thereof; is one or both of tetraisopropyl titanate and tetrabutyl titanate.

In an embodiment, the amounts of the catalyst in step I and step II are respectively 0.05% to 0.5% of, 0.06% to 0.2% of, 0.07% to 0.1% of, 0.07% to 0.09% of the total mass of the bio-based dibasic acid or ester containing a furan structure, the bio-based aliphatic dibasic acid or ester, the bio-based diol, and the bio-based polyethylene glycol.

According to some specific implementations, the catalyst in step I is an organic titanate catalyst, and the catalyst in step II is an acetate metal salt.

According to another implementation, the preparation method of a bio-based moisture absorption and sweat discharging multifunctional finishing agent specifically comprises: performing a first reaction between the bio-based dibasic acid or ester containing a furan structure, the bio-based aliphatic dibasic acid or ester, the bio-based diol and the bio-based polyethylene glycol under the action of a catalyst to obtain a transesterification prepolymer product; then adjusting the temperature to undergo a second reaction, and then vacuumizing to perform a third polycondensation reaction to give the bio-based moisture absorption and sweat discharging multifunctional finishing agent.

In an embodiment, the reaction temperature and conditions of the first reaction are the same as those of step I; the reaction temperature and conditions of the second reaction are the same as those of step II; the reaction temperature and conditions of the third polycondensation reaction are the same as those of step III.

A further aspect of the present disclosure provides an application of a bio-based moisture absorption and sweat discharging multifunctional finishing agent in hydrophobic fiber fabrics.

In an embodiment, hydrophobic fibers in the hydrophobic fiber fabrics comprise one or more selected from polyester, spandex, acrylic, and polyamide; is polyester.

Due to the use of the above technical solutions, the present disclosure has the following advantages over the conventional art:

The bio-based moisture absorption and sweat discharging multifunctional finishing agent of the present disclosure is sourced from bio-based materials, replaces traditional petroleum-based chemical raw materials, reduces dependence on petroleum resources, embraces the development of a Carbon Peaking and Carbon Neutralization policies, and fills the gap in the market for bio-based moisture absorption and sweat discharging multifunctional finishing agents. In addition, its use in the after finish of hydrophobic fiber fabrics can improve their water absorption and anti-static properties, giving them a laundering durable effect and a fluffy and soft feel.

DETAILED DESCRIPTION OF EXEMPLARY EMBODIMENTS

All the features disclosed in the present disclosure, or all the steps in the disclosed methods or processes, except for mutually exclusive features or steps, can be combined in any way.

Given the shortcomings in the conventional art, the inventors of this case have been able to propose the technical solutions of the present disclosure through long-term research and extensive practice. The following will provide further explanations on the technical solutions, their implementation process, and principles.

2,5-furandicarboxylic acid (FDCA) is a renewable and green substitute for terephthalic acid and can be widely used as a precursor for the synthesis of bio-based polyesters and various other polymers. Compared with petroleum-based poly(ethylene terephthalate) (PET), bio-based polyester-poly(ethylene 2,5-furandicarboxylate) (PEF) has better physical-mechanical properties, higher thermal stability, and better molecular flexibility. Avantium, a Dutch company, has confirmed that PEF (poly(ethylene 2,5-furandicarboxylate)) can be used to make fibers, and even recycled PEF bottles can be made into PEF fibers, these fibers can be processed into 100% bio-based T-shirts, however, in the field of engineering plastics, if used in the preparation of beverage bottles, it is required to have excellent hydrophobicity.

At present, the preparation of bio-based moisture absorption and sweat discharging finishing agents for hydrophobic fiber fabrics using bio-based materials is still in the blank stage at home and abroad.

In the present disclosure, through directly carrying out an esterification reaction of bio-based dibasic acids containing a furan structure and bio-based aliphatic dibasic acids with bio-based diol under the action of a catalyst, or directly carrying out a transesterification reaction of bio-based dibasic esters containing a furan structure and bio-based aliphatic dibasic esters with bio-based diol under the action of a catalyst, diol 2,5-furandicarboxylate chain segments and diol succinate chain segments, for example, ethylene glycol 2,5-furandicarboxylate chain segments, ethylene glycol succinate chain segments, propylene glycol 2,5-furandicarboxylate chain segments, butylene glycol 2,5-furandicarboxylate chain segments, propylene glycol succinate chain segments and butylene glycol succinate chain segments, are prepared, and then undergoes a transesterification reaction with bio-based polyethylene glycol to prepare a transesterification prepolymer product, which finally undergoes a polycondensation reaction to give a bio-based moisture absorption and sweat discharging multifunctional finishing agent. The bio-based moisture absorption and sweat discharging multifunctional finishing agent takes the bio-based diol 2,5-furandicarboxylate chain segments with an aromatic ring structure as the main chain core, and introduces the semi-crystalline diol succinate chain segments with good flexibility, and then hydrophilic segments such as bio-based polyethylene glycol are embedded alternately, making use of the molecular activity of each block unit, the force between molecules, the flexibility of molecular chains, the properties of the groups and the like to create synergistic effects with each other to achieve the multifunctionality of the finishing agent. Th hydrophobic fiber fabrics treated with this finishing agent, in particular polyester fiber fabrics, have excellent moisture absorption, sweat discharging, anti-static properties, easy-cleaning property, laundering durability, soft and fluffy hand feel, etc., which enable them to achieve multiple functions in one finish, and can improve the ecological environment to achieve low-carbon economy. In addition, the segmented polymerization is adopted to maintain the stability of polymerization raw material components, with less by-products and easy control, and good molecular structure regularity, thus ensuring the stability of product performance.

Furthermore, the structure of the bio-based moisture absorbing and sweat discharging multifunctional finishing agent has 3 to 6 structural units, especially the addition of bio-based aliphatic dibasic acid functional groups or bio-based aliphatic dibasic ester functional groups can be blocked, alternately, or statistically distributed, a single polyethylene glycol with a weight-average molecular weight range of 2000-4000 g/mol is synergistically used as a hydrophilic macromonomer, and avoid using a mixture of two or more polyethylene glycols, in this way, a finishing agent with a narrower molecular weight distribution is obtained, while its laundering durability is improved.

Furthermore, the structure of the finishing agent in the present disclosure contains bio-based polyester chain segments that have good compatibility with fiber polyester, promoting the formation of a good boundary layer with various hydrophilic polyether chain segments on the surface of polyester fibers, which not only effectively solves the moisture absorption and sweat discharging properties of polyester fiber materials, but also gives the fiber fabrics with characteristics such as a fluffy and soft hand feel and laundering durability.

The present disclosure is further described below combining with embodiments. But the present disclosure is not limited to the embodiments below. The implementation conditions used in the embodiments may be further adjusted according to different requirements of specific use, and undefined implementation conditions usually are conventional conditions in the industry. The technical features involved in the various embodiments of the present disclosure may be combined with each other if they do not conflict with each other.

The experimental methods in the following embodiments, unless otherwise specified, are all conventional methods; the experimental materials used, unless otherwise specified, can be obtained through commercial procurement and/or by known means, and unless otherwise specified, they all meet the requirements for standardized chemical products.

In the experimental methods in the following embodiments, the parts of each substance refer to the parts by weight.

Embodiment 1

This embodiment provided a bio-based moisture absorption and sweat discharging multifunctional finishing agent, which was prepared using the following process:
(1) 20.8 parts of bio-based 2,5-furandicarboxylic acid, 9.7 parts of bio-based succinic acid, 23 parts of bio-based 1,3-propanediol, 12 parts of bio-based ethylene glycol, and 0.3 parts of tetrabutyl titanate were added to a reactor successively, and under nitrogen protection, the system was gradually heated to 180° C. to react for 1 hour, and then heated to 200° C. to react for 2 to 2.5 hours, and when the water yield reached 90% of the theoretical water yield, an esterification product was obtained;
(2) In the esterification product, 320 parts of bio-based polyethylene glycol (PEG4000) and 0.3 parts of sodium acetate were added, and under nitrogen protection, the system was gradually heated to 220° C. to react for 1 hour, and then heated to 245° C. to react for 1.5 hours to obtain a transesterification prepolymer product;
(3) The transesterification prepolymer product was reacted for 3 hours under a vacuum degree of 0.095 to 0.1 MPa and a temperature of 260° C. to give a bio-based moisture absorption and sweat discharging multifunctional finishing agent.

Embodiment 2

This embodiment provided a bio-based moisture absorption and sweat discharging multifunctional finishing agent, which was prepared using the following process:
(1) 24.8 parts of bio-based 2,5-furandicarboxylic acid, 4.7 parts of bio-based succinic acid, 17 parts of bio-based 1,3-propanediol, 17 parts of bio-based ethylene glycol, and 0.3 parts of tetrabutyl titanate were added to a reactor successively, and under nitrogen protection, the system was gradually heated to 180° C. to react for 1 hour, and then heated to 200° C. to react for 2 to 2.5 hours, and when the water yield reached 90% of the theoretical water yield, an esterification product was obtained;
(2) In the esterification product, 320 parts of bio-based polyethylene glycol (PEG4000) and 0.3 parts of sodium acetate were added, and under nitrogen protection, the system was gradually heated to 220° C. to react for 1 hour, and then heated to 245° C. to react for 1.5 hours to obtain a transesterification prepolymer product;
(3) The transesterification prepolymer product was reacted for 3 hours under a vacuum degree of 0.095 to 0.1 MPa and a temperature of 260° C. to give a bio-based moisture absorption and sweat discharging multifunctional finishing agent.

Embodiment 3

This embodiment provided a bio-based moisture absorption and sweat discharging multifunctional finishing agent, which was prepared using the following process:
(1) 24.8 parts of bio-based 2,5-furandicarboxylic acid, 4.7 parts of bio-based succinic acid, 18 parts of bio-based 1,4-butanediol, 18 parts of bio-based ethylene glycol, and 0.3 parts of tetraisopropyl titanate were added to a reactor successively, and under nitrogen protection, the system was gradually heated to 180° C. to react for 1 hour, and then heated to 200° C. to react for 2 to 2.5 hours, and when the water yield reached 90% of the theoretical water yield, an esterification product was obtained;
(2) In the esterification product, 280 parts of bio-based polyethylene glycol (PEG2000) and 0.3 parts of sodium acetate were added, and under nitrogen protection, the system was gradually heated to 220° C. to react for 1 hour, and then heated to 245° C. to react for 2 hours to obtain a transesterification prepolymer product;
(3) The transesterification prepolymer product was reacted for 3.5 hours under a vacuum degree of 0.095 to 0.1 MPa and a temperature of 260° C. to give a bio-based moisture absorption and sweat discharging multifunctional finishing agent.

Embodiment 4

This embodiment provided a bio-based moisture absorption and sweat discharging multifunctional finishing agent, which was prepared using the following process:
(1) 24.5 parts of bio-based dimethyl furan-2,5-dicarboxylate, 12 parts of bio-based dimethyl succinate, 23 parts of bio-based 1,3-propanediol, 12 parts of bio-based ethylene glycol, 320 parts of bio-based polyethylene glycol (PEG4000), 0.3 parts of sodium acetate, and 0.3 parts of tetrabutyl titanate were added to a reactor successively, and under nitrogen protection, the system was gradually heated to 180° C. to react for 1 hour, and then heated to 200° C. to react for 2 to 2.5 hours, and when the actual amount of methanol distilled reached 90% of the theoretical amount of methanol, a transesterification prepolymer product was obtained;
(2) The transesterification prepolymer product was gradually heated to 220° C. to react for 1 hour, then heated to 245° C. to react for 1.5 hours, and then reacted for 3 hours under a vacuum degree of 0.095 to 0.1 MPa and a temperature of 260° C. to give a bio-based moisture absorption and sweat discharging multifunctional finishing agent.

Comparative Example 1

This comparative example provided a finishing agent, which was prepared using the following process:
(1) 31 parts of bio-based 2,5-furandicarboxylic acid, 30.8 parts of bio-based ethylene glycol, and 0.3 parts of tetrabutyl titanate were added to a reactor successively, and under nitrogen protection, the system was gradually heated to 180° C. to react for 1 hour, and then heated to 210° C. to react for 2 to 2.5 hours, and when the water yield reached 90% of the theoretical water yield, the reaction was completed, and an esterification product was obtained;
(2) In the esterification product, 280 parts of bio-based polyether (PEG4000) and 0.3 parts of sodium acetate were added, and under nitrogen protection, the system was gradually heated to 220° C. to react for 1 hour, and then heated to 245° C. to react for 1.5 hours to obtain a transesterification prepolymer product;
(3) The transesterification prepolymer product was reacted for 3 hours under a vacuum degree of 0.095 to 0.1 MPa and a temperature of 260° C. to give a finishing agent.

Comparative Example 2

This comparative example provided a finishing agent, which was prepared using the following process:
(1) 38.8 parts of dimethyl terephthalate, 30.8 parts of bio-based ethylene glycol, 360 parts of bio-based polyethylene glycol (PEG4000), 0.3 parts of sodium acetate, and 0.3 parts of tetrabutyl titanate were added to a reactor successively, and under nitrogen protection, the system was gradually heated to 180° C. to react for 1 hour, and then heated to 245° C. to react for 5 hours, and when the actual amount of methanol reached 90% of the theoretical amount of methanol, a transesterification prepolymer product was obtained;
(2) The transesterification prepolymer product was gradually heated to 220° C. to react for 1 hour, then heated to 245° C. to react for 1.5 hours, and then reacted for 3 hours under a vacuum degree of 0.095 to 0.1 MPa and a temperature of 260° C. to give a finishing agent.

Performance Tests

The polyester fiber fabrics were treated with the finishing agents of Embodiments 1-4, the finishing agents of Comparative examples 1-2, and market non-biological based moisture absorption and sweat discharging finishing agent (a polyester moisture absorption and sweat discharging finishing agent SRS—W purchased from Wuxi Haiyunhua Chemical Co., Ltd.), respectively, and the experimental process for the treatment was as follows: soaking twice and rolling twice (with a liquid content of 70%)—drying (105° C.)—heat setting (180° C., 60 s), and the blank fabric was a polyester fiber fabric that had not undergone any treatment.

The treated polyester fiber fabrics were tested for moisture absorption, quick drying, hydrophilicity, laundering durability, and soft and fluffy hand feel.
(1) Moisture absorption and sweat discharging performance test: Refer to methods in the national standard GB/T 21655.1-2008 *Textiles—Evaluation of absorption and quick-drying*.

Principle: Characterize the fabric's ability to adsorb liquid sweat (hygroscopicity) based on the wicking height of the fabric and the drip diffusion time. Specifically, the hydrophilicity was evaluated based on the wicking height at 30 min of polyester fabric treated with a finishing agent, the larger the wicking height value, the better the hydrophilicity and moisture absorption, and at the same time, a blank control test was conducted on polyester fabric not treated with a finishing agent.

The standard fabric was polyester knitted fabric (75D/72F, 140 g/m$^2$);

The laundering durability test followed the AATCC135 American standard washing program. This program requires a washing time of 25 min each time (including 15 min of washing, 4 min of rinsing, and 6 min of dehydration).

The specific test results are shown in Tables 1 and 2.

TABLE 1

| | Wicking height test results (mm/30 min) | | | |
|---|---|---|---|---|
| Finishing agents | Before washing | Wash 10 times with water | Wash 20 times with water | Wash 30 times with water |
| Blank fabric | 45 | 47 | 50 | 52 |
| Embodiment 1 | 255 | 248 | 220 | 198 |
| Embodiment 2 | 252 | 243 | 219 | 186 |
| Embodiment 3 | 248 | 236 | 210 | 181 |
| Embodiment 4 | 253 | 245 | 213 | 195 |
| Comparative example 1 | 224 | 180 | 135 | 112 |
| Comparative example 2 | 232 | 115 | 91 | 81 |
| Market product | 230 | 102 | 82 | 79 |

Note: The larger the wicking height value, the better the hydrophilicity and moisture absorption.

TABLE 2

| | Drip diffusion time test results | | | |
|---|---|---|---|---|
| Finishing agents | Before washing | Wash 10 times with water | Wash 20 times with water | Wash 30 times with water |
| Blank fabric | >180 s | >180 s | >180 s | >180 s |
| Embodiment 1 | <1 s | <1 s | <1 s | <1 s |
| Embodiment 2 | <1 s | <1 s | <1 s | <1 s |
| Embodiment 3 | <1 s | <1 s | <1 s | 2.1 s |
| Embodiment 4 | <1 s | <1 s | <1 s | <1 s |
| Comparative example 1 | <1 s | <1 s | 5.9 s | 8.9 s |
| Comparative example 2 | <1 s | 8.2 s | 20.5 s | 40.2 s |
| Market product | <1 s | 9.1 s | 33.2 s | 51.6 s |

Note: The drip diffusion time of water is measured in seconds (s), and the shorter the drip diffusion time of water, the better the hygroscopicity, data <1 s indicates instantaneous absorption.

(2) Quick-drying performance test: Refer to methods in the national standard GB/T 21655.1-2008 *Textiles— Evaluation of absorption and quick-drying.*

Principle: Characterize the quick drying (sweat discharging) of a fabric in a liquid sweat state by measuring its residual moisture evaporation rate under specified air conditions. The quick drying performance is represented by the residual rate after water evaporation, and the lower the residual rate of water, the better the quick drying performance.

The specific method was, according to the determination method for water evaporation rate and evaporation time in Section 8.3 of the national standard, testing the specific water evaporation amount for 10 min, 20 min, 30 min, 40 min, 50 min, and 60 min, and calculating the water residue rate in the fabric based on the weight ratio of the fabric before and after evaporation.

The test results are shown in Table 3.

TABLE 3

Water residue rate test results

| Finishing agents | Water residue rate % | | | | | |
|---|---|---|---|---|---|---|
| | 10 min | 20 min | 30 min | 40 min | 50 min | 60 min |
| Blank fabric | 97.50 | 94.50 | 90.00 | 87.00 | 82.50 | 79.50 |
| Embodiment 1 | 71.57 | 55.15 | 43.73 | 26.82 | 15.39 | 4.56 |
| Embodiment 2 | 74.96 | 57.56 | 46.23 | 28.56 | 16.68 | 5.86 |
| Embodiment 3 | 76.00 | 59.86 | 48.96 | 30.20 | 17.36 | 6.20 |
| Embodiment 4 | 71.80 | 55.68 | 44.00 | 27.12 | 15.87 | 4.96 |
| Comparative example 1 | 84.68 | 65.26 | 58.34 | 49.88 | 35.00 | 18.12 |
| Comparative example 2 | 89.65 | 70.88 | 68.34 | 56.11 | 45.25 | 34.12 |
| Market product | 89.94 | 71.65 | 69.15 | 59.71 | 49.89 | 45.67 |

(3) Hand feel test:

The tactile rating method was conducted by experienced five people, with scores ranging from 1 to 5 indicating the comparison of tactile results, 5 indicating the best, and 1 indicating the worst.

The test results are shown in Table 4.

TABLE 4

Hand feel performance test results

| Finishing agents | Terry fabric | | All-polyester knitted fabric | | All-polyester smooth shuttle fabric | | Coral fabric | |
|---|---|---|---|---|---|---|---|---|
| | Soft | Fluffy | Soft | Fluffy | Soft | Fluffy | Soft | Fluffy |
| Blank fabric | 1 | 1 | 1 | 1 | 1 | 1 | 1 | 1 |
| Embodiment 1 | 4-5 | 4 | 4-5 | 4 | 4-5 | 4 | 4-5 | 4 |
| Embodiment 2 | 4-5 | 4 | 4-5 | 4 | 4-5 | 4 | 4 | 4 |
| Embodiment 3 | 4 | 4 | 4 | 3-4 | 4 | 3-4 | 4 | 3-4 |
| Embodiment 4 | 4-5 | 4 | 4-5 | 4 | 4-5 | 4 | 4-5 | 4 |
| Comparative example 1 | 3-4 | 3 | 3-4 | 3 | 3-4 | 2-3 | 3-4 | 2-3 |
| Comparative example 2 | 3 | 2-3 | 3 | 2-3 | 3 | 3 | 3 | 3 |
| Market product | 3 | 2-3 | 3 | 2-3 | 3 | 2-3 | 3 | 2-3 |

The polyester fiber fabrics treated with the bio-based moisture absorption and sweat discharging multifunctional finishing agent of the present disclosure has excellent moisture absorption and sweat discharging performance, laundering durability, and a soft and flufiry hand feel, and overcomes the problem that non-biological based moisture absorption and sweat discharging finishing agents on the market cannot balance hydrophilicity and hand feel. The experimental data shows that the bio-based moisture absorption and sweat discharging multifunctional finishing agent of the present disclosure is superior to the petroleum-based moisture absorption and sweat discharging hydrophilic finishing agent products, and has broad market prospects.

Although the present invention has been disclosed in the form of embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

What is claimed is:

1. A bio-based moisture absorption and sweat discharging multifunctional finishing agent having the following structural formula:

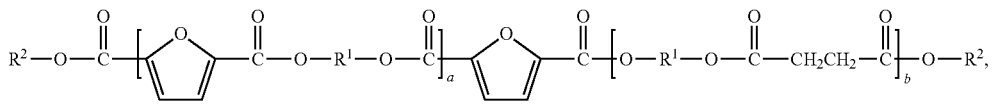

wherein, $R^1$ is linear or branched alkyl;

$R^2$ is derived from bio-based polyethylene glycol, with a molecular structure of $-(CH_2CH_2O)_n-H$, n=22 to 91, and n is a natural number;

a=60 to 150, a is a natural number; b is a natural number;

the molar ratio of structural units with a degree of polymerization of a to those with a degree of polymerization of b is (30 to 85):(15 to 40).

2. The bio-based moisture absorption and sweat discharging multifunctional finishing agent of claim 1, $R^1$ is $-(CH_2)_c-$, c=2 to 4, c is a natural number; and/or, in the structural formula of the bio-based moisture absorption and sweat discharging multifunctional finishing agent, the molar ratio of structural units with a degree of polymerization of a to those with a degree of polymerization of b is (30 to 80):(20 to 40).

3. The bio-based moisture absorption and sweat discharging multifunctional finishing agent of claim 1, wherein in the structural formula of the bio-based moisture absorption and sweat discharging multifunctional finishing agent, the structural units with a degree of polymerization of a and a degree of polymerization of b are blocked, alternately, or statistically distributed.

4. The bio-based moisture absorption and sweat discharging multifunctional finishing agent of claim 1, wherein $R^1$ in the structural units with a degree of polymerization of a is the same as or different from that of the structural units with a degree of polymerization of b, $R^1$ is derived from a corresponding bio-based diol, and the molecular structure of the bio-based diol is $HO-(CH_2)_c-OH$, c=2 to 4, c is a natural number; and/or, the bio-based moisture absorption and sweat discharging multifunctional finishing agent after polymerization has a weight-average molecular weight of 8000~30000 g/mol.

5. The bio-based moisture absorption and sweat discharging multifunctional finishing agent of claim 1, wherein the raw materials for preparation of the bio-based moisture absorption and sweat discharging multifunctional finishing agent comprises: a bio-based dibasic acid or ester containing a furan structure, a bio-based aliphatic dibasic acid or ester, a bio-based diol, and bio-based polyethylene glycol.

6. The bio-based moisture absorption and sweat discharging multifunctional finishing agent of claim 5, wherein the bio-based dibasic acid or ester containing a furan structure is bio-based 2,5-furandicarboxylic acid or bio-based dimethyl furan-2,5-dicarboxylate, and the bio-based aliphatic dibasic acid or ester is bio-based succinic acid or bio-based dimethyl succinate; and/or, the bio-based diol is selected from the group consisting of bio-based 1,3-propanediol, bio-based ethylene glycol, bio-based 1,4-butanediol, and combinations thereof.

7. The bio-based moisture absorption and sweat discharging multifunctional finishing agent of claim 5, wherein the bio-based diol is bio-based ethylene glycol and bio-based 1,3-propanediol, or, the bio-based diol is bio-based ethylene glycol and bio-based 1,4-butanediol; and/or, the bio-based polyethylene glycol is bio-based polyethylene glycol with a weight-average molecular weight of 1000 to 4000 g/mol.

8. A preparation method of a bio-based moisture absorption and sweat discharging multifunctional finishing agent of claim 1, comprising steps of:
(1) reacting a bio-based dibasic acid or ester containing a furan structure, a bio-based aliphatic dibasic acid or ester, a bio-based diol with bio-based polyethylene glycol under the action of a catalyst to obtain a transesterification prepolymer product;
(2) making the transesterification prepolymer product obtained in step (1) under evacuation to undergo a polycondensation reaction to give the bio-based moisture absorption and sweat discharging multifunctional finishing agent;

in step (1), the bio-based polyethylene glycol is added in the same procedure with the bio-based dibasic acid or ester containing a furan structure, the bio-based aliphatic dibasic acid or ester and the bio-based diol to react to give the transesterification prepolymer product;
or, the bio-based polyethylene glycol is added after the bio-based dibasic acid or ester containing a furan structure, the bio-based aliphatic dibasic acid or ester and the bio-based diol are reacted to obtain an intermediate product, and then the reaction continues to give the transesterification prepolymer product.

9. The preparation method of a bio-based moisture absorption and sweat discharging multifunctional finishing agent of claim 8, wherein the preparation method of a biobased moisture absorption and sweat discharging multifunctional finishing agent comprises:
step I: reacting the bio-based dibasic acid or ester containing a furan structure, the bio-based aliphatic dibasic acid or ester and the bio-based diol under the action of a catalyst to obtain an intermediate product;
step II: performing a transesterification reaction between bio-based polyethylene glycol and the intermediate product obtained in step I under the action of a catalyst to obtain a transesterification prepolymer product;
step III: making the transesterification prepolymer product obtained in step II under evacuation to undergo a polycondensation reaction to give the bio-based moisture absorption and sweat discharging multifunctional finishing agent.

10. The preparation method of a bio-based moisture absorption and sweat discharging multifunctional finishing agent of claim 8, having a feeding weight ratio of the biobased dibasic acid or ester containing a furan structure, the bio-based aliphatic dibasic acid or ester, the bio-based diol, and the bio-based polyethylene glycol is 1:(0.1 to 2):(0.9 to 3.6):(5 to 40).

11. The preparation method of a bio-based moisture absorption and sweat discharging multifunctional finishing agent of claim 9, wherein in step I, a temperature of the reaction is controlled at 150~220° C. and a reaction time is controlled at 3~5 hours; and/or, in step II, a temperature of the transesterification reaction is controlled at 180~250° C. and a reaction time is controlled at 2~5 hours; and/or, in step III, a temperature of the polycondensation reaction is controlled at 240 to 280° C., a vacuum degree is controlled at 0.05 to 0.1 MPa and a reaction time is controlled at 3 to 5 hours.

12. A method of finishing hydrophobic fiber fabrics, the method comprising: utilizing the bio-based moisture absorption and sweat discharging multifunctional finishing agent of claim 1.

13. The method of claim 12, wherein hydrophobic fibers in the hydrophobic fiber fabrics comprise one or more selected from polyester, spandex, acrylic, and polyamide.

* * * * *